United States Patent [19]

Gergely et al.

[11] Patent Number: 5,260,304
[45] Date of Patent: Nov. 9, 1993

[54] PHARMACEUTICAL PREPARATION BINDING WITH GASTRIC ACID

[76] Inventors: Gerhard Gergely; Thomas Gergely; Irmgard Gergely, all of Gartengasse 8, A-1050 Vienna, Austria

[21] Appl. No.: 838,435

[22] PCT Filed: Sep. 6, 1990

[86] PCT No.: PCT/EP90/01503
§ 371 Date: Mar. 6, 1992
§ 102(e) Date: Mar. 6, 1992

[87] PCT Pub. No.: WO91/03241
PCT Pub. Date: Mar. 21, 1991

[30] Foreign Application Priority Data

Sep. 7, 1989 [CH] Switzerland ............... 3260/89
Sep. 15, 1989 [CH] Switzerland ............... 3366/89
Feb. 20, 1990 [CH] Switzerland ............... 532/90

[51] Int. Cl.$^5$ .............. A61K 31/29; A61K 9/16; A61K 9/46; A61K 33/24; A23L 2/40
[52] U.S. Cl. .......................... 514/58; 424/43; 424/44; 424/464; 424/466; 424/470; 424/474; 424/479; 424/489; 424/493; 514/54; 514/474; 514/777; 514/819
[58] Field of Search ........ 514/819, 474, 777, 54, 514/58; 424/43, 466, 470, 489, 493, 44, 464, 474, 479

[56] References Cited

U.S. PATENT DOCUMENTS 4,678,661 7/1987 Gergely et al. ............... 424/44
4,801,454 1/1989 Conveney ............... 514/503

FOREIGN PATENT DOCUMENTS 85376 8/1983 European Pat. Off. .
181564 5/1986 European Pat. Off. .
286085 10/1988 European Pat. Off. .
514888 11/1939 United Kingdom .
524756 8/1940 United Kingdom .
WO88/00009 1/1988 World Int. Prop. O. .

Primary Examiner—Ronald W. Griffin
Attorney, Agent, or Firm—Ostrolenk, Faber, Gerb & Soffen

[57] ABSTRACT

Granules, possibly pressed into the form of tablets, contain at least one insoluble, complexed or slightly soluble active substance in powder form which can bind or neutralize acids and which does not react with the acid of the effervescent system, and an effervescent system consisting of at least one organic, edible acid and at least one alkali metal and/or alkaline earth metal carbonate and/or bicarbonate. The active substance is present in an amount of 5 to 50, preferably 8 to 30, in particular 12 to 25%, by weight. It has an acid binding power of 2 to 40, preferably 3.5 to 25, meq/g, does not react with the acid of the effervescent system and increases the pH in 0.1N HCl during 2 min by a maximum of 0.5. It consists in particular of magnesium trisilicate, sucralfate and/or a bismuth salt. Each granule contains at least one acid component, at least one carbonate component and at least one active substance bound to one another. Binding of the granule components to one another is effected by a reaction product of an acidic with a carbonate component and/or by at least one hydrocolloid, in particular xanthan, maltodextrin, galactomanan and/or tragacanth.

16 Claims, No Drawings

PHARMACEUTICAL PREPARATION BINDING WITH GASTRIC ACID

The invention relates to a pharmaceutical preparation for use for in connection with gastric acid.

There are many known systems which buffer gastric acid, especially in the case of hyperacidity or an ulcer, in order to reduce the attacks by the hydrochloric acid on the stomach wall. However, most systems suffer from the so-called "rebound effect": if the gastric acid is buffered, the stomach produces additional amounts of acid and the effect is reversed. This refers in particular to the preparations which are taken in tablet form, because in this case there is also the effect of local concentrations during dissolution of the tablet in the stomach.

Here, the effervescent tablet is a particular form of a gastric buffer. The buffer system of many effervescent tablets serves for neutralizing the hydrochloric acid of the stomach, especially in the case of hyperacidity. This buffer capacity is measured as the acid binding power, is stated in meq of HCl and is standardized in most countries. For example, in a conventional buffer effervescent tablet it is not so much the acetylsalicylic acid, which is also present, but the buffer system that acts against hangovers.

There are a number of active substances which, in addition to buffering the gastric acid, have a prolonged effect of protecting the stomach wall, and which are administered in the form of lozenges, chewable tablets or an aqueous suspension.

Gastric buffer systems have to date generally been combinations which contain aluminum hydroxide and/or magnesium salts, which were administered as chewable tablets or as an emulsion or suspension and are widely used in all countries because hyperacidity is a disease of modern civilization.

Gastric and intestinal diseases, such as, for example, gastritis, enteritis, etc., have also frequently been treated with bismuth-containing medicaments. However, the bismuth therapy has various disadvantages:

Soluble bismuth compounds, including those which are merely in colloidal solutions, as administered, for example, in the form of syrup, frequently lead to unpleasant colorations on the teeth. The latter of course also applies to chewable tablets or lozenges which remain in the oral and pharyngal cavity for long times.

Bismuth-containing tablets, particularly if they are coated, or capsules do not have this disadvantage but may lead to an excessive local concentration on arriving at, and reacting with, the mucus membrane of the intestinal tract, and are toxic above certain amounts, in particular if they immediately come into contact in high concentration with certain areas of the gastric and/or intestinal mucus membrane.

Suspensions based on magnesium trisilicate (administered in particular for gastritis), sucralfate or insoluble bismuth salts appear to be the most effective. However, such effervescent tablets, which already have a very high buffer capacity, have the problem that the active substances, which are water-insoluble powders, are difficult to suspend in the solution. When the tablet is introduced into water, it effervesces but, after complete dissolution, a thick layer of the active ingredient lies at the bottom of the glass and has to be resuspended by stirring.

It is the object of the invention to provide a pharmaceutical preparation in the form of effervescent granules or of an effervescent tablet which avoids the stated disadvantages and, on dissolution in water, gives a suspension of the insoluble or very slightly soluble active substances or antacid substances in water, which suspension is stable for at least a few minutes. This is associated with further advantages of improved intake in the form of a solution which is pleasant to drink, as well as of a good flavor of the active substance and good acceptance.

The further objects of the invention are to provide a form for the administration of bismuth compounds which reaches the various areas of the gastric or intestinal mucus membranes in very finely divided form without the formation of local excess concentrations. These objects are achieved, surprisingly, by the measures described herein.

The acid binding power is measured according to ASTM in such a way that 1 g of pulverized active substance is stirred in 30 ml of 0.1N HCl for 15 min at room temperature after which back titration is carried out with 0.1N NaOH to a pH of 3.5, which must remain stable for 10 sec.

Although EP-A1-286085 has already described a gastric acid-binding composition consisting of a water-soluble substance, such as pectin or cellulose derivatives, which are gel-binding at acidic pH, in combination with a buffer substance which is dispersed in the gel, such as, for example, casein, and an acid-neutralizing substance which has a foam-forming or stabilizing effect on contact with the gastric acid (magnesium carbonate, potassium carbonate), the principal reaction differs from that of the present invention.

U.S. Pat. No. 4,801,454 describes a non-effervescent preparation which is commercially available as a prepared suspension and which is obtained by the treatment of an—optionally insoluble—bismuth compound with a dye. However, such a bismuth compound without a buffer system and in a relatively high concentration has the disadvantages described at the outset.

GB-A-514,888 describes a process in which magnesium hydroxide is mixed with sodium bicarbonate, citric acid and tartaric acid and then heated to 95°–105° C. to eliminate the water of crystallization of the citric acid, the procedure giving a paste which is subsequently sieved and may be dried and, after further comminution, is pressed to give granules or tablets. If such effervescent granules or such an effervescent tablet is added to water, only slow effervescence occurs because, owing to the higher pH, the magnesium hydroxide partially interferes with the reaction of the effervescent components or itself partially reacts with the acidic components to give soluble magnesium salts and, as a result of the slow reaction, the magnesium hydroxide sinks to the bottom. Moreover, magnesium hydroxide also results in immediate neutralization of the gastric acid at the stomach wall, as in the case of other alkaline substances, and thus also entails the danger of the stated rebound effect.

Although EP-A2-85376 refers to effervescent systems containing any active substances, it mentions exclusively agrochemical and veterinary/pharmaceutical systems; nothing in the disclosure indicates to the skilled worker the combination according to the invention.

According to the invention, it is important that an antacid which is slightly soluble, complex or insoluble and reacts with none of the effervescent components, or such an active substance, such as, for example, magnesium trisilicate, sucralfate or a bismuth salt, is used in very finely pulverized form so that, when mixed with the also very finely pulverized carbonate, it is anchored on the surface of individual crystals of an edible organic acid. This has a plurality of advantages all at once over the prior art:

1. The effervescent reaction is not delayed; the effervescent tablet or the granules dissolve rapidly and the suspension can be drunk before the active substance particles have settled out.

2. On dissolution of the tablet, the active substance is suspended in a buffer solution formed from citric acid and the alkali metal carbonates or bicarbonates.

3. The active substance reaches the stomach wall without undergoing a reaction and in a very finely divided form and forms on this wall a film which, on the one hand, neutralizes the gastric acid slowly and partly through gel formation and, on the other hand, develops its specific activity and thus prevents the rebound effect.

The particular advantage of such systems is that the effervescent tablet is used not only for suspending the active substance during dissolution in water but, by means of the alkali metal bicarbonates or alkaline earth metal carbonates, additionally achieves a rapid, efficient and effective buffering of the gastric acid and furthermore the non-reactive active substances, such as, for example, magnesium trisilicate or sucralfate, slowly and gradually neutralize the acid produced by the stomach wall or display their specific activity, such as, for example, gel formation or a bactericidal action.

Virtually all insoluble or slightly soluble bismuth salts with pharmaceutically permissible anions, such as, for example, bismuth hydroxide, bismuth subnitrate, bismuth oxide, bismuth subcarbonate, bismuth subgallate and bismuth subsalicylate, as well as mixtures of these or similar bismuth salts are also suitable.

In particular, this also avoids local concentrations, as occur when taking tablets or chewable tablets, which may then develop a particularly strong irritant effect at specific points where they act on the stomach wall. This irritant effect is completely absent in the case of the preparation according to the invention.

The suspension behavior is improved if hydrocolloids, such as, for example, traganth, guar gum or dextrins, such as maltodextrin, etc., or a galactomanan are added to these systems. Their function is to make the water slightly more dense, to accumulate around the particles and to prevent the latter from sinking or from coagulating. If such hydrocolloids are incorporated into the system in a suitable manner, dissolution of the effervescent tablet results in a perfect suspension of the water-insoluble active substance, which remains stable for many minutes and can be conveniently taken.

The hydrocolloids incorporated into a mixture generally prolong the dissolution time of an effervescent system by causing the tablet to stick together when moisture is admitted. On the other hand, relatively small amounts can have a wick effect by conducting moisture into the interior of the tablet. These are maltodextrins in an amount of 1-5%, gelatine or gum arabic, which are less useful but may also be employed in an amount of 2-3%.

First, it is possible for the active substances to be incorporated into the effervescent system by means of granules, which can be produced both by a normal method but more advantageously by the vacuum method, so that the substances are automatically suspended during effervescence of the tablet.

According to the invention, such insoluble or slightly soluble salts can be uniformly suspended in about 100 to 150 ml of water by the effervescent effect of effervescent tablets having 2 to 4 g in the course of the dissolution time and can be taken as a pleasant-tasting suspension. The finer these particles, the more extensively and completely is the stomach wall covered with relatively low doses.

At the same time, with the corresponding formulation of the effervescent tablet it is possible to produce a buffer system which initially buffers the free gastric acid, with the result that a rapid and effective function can be achieved. In the case of bismuth salts, an oligodynamic effect, as is also known for silver, very probably takes place, the oligodynamics being achieved by traces of metals or metal salts in the water. The metal activity may be responsible, for example, for the action of bismuth on Campylobacter pylori. The very finely divided, particularly insoluble particles or complex molecules of the bismuth salt then serve for covering the stomach walls.

It is in fact particularly advantageous if bismuth is present in complexed form, such as, for example, in potassium bismuth citrate. Complexes which are decomposed only at very low pH promote uniform distribution in the gastrointestinal tract and permit very small doses. The stated combination with a buffer system counteracts the undesirably rapid destruction of the complex.

The invention may also, and in particular, be applied in the case of persons who suffer from hyperacidity and produce a relatively large amount of gastric acid. The toxic symptoms observed to date in the case of bismuth salts may be due to the large amounts of dissolved bismuth salts, possibly also to the bismuth chloride formed. Relatively large amounts of gastric acid, as formed in the case of gastritis, may also be buffered by the accompanying buffer solution of the effervescent tablet.

According to the invention, the undesired supply of sodium ions may furthermore be increased by using potassium- and calcium-containing effervescent mixtures.

Suitable precautions for effervescent solutions and ad hoc suspensions are an effervescent effect which is not exaggerated, i.e. which takes place slowly, so that the particles can be well distributed, in the stated presence of colloids.

The invention is explained in detail below with reference to Examples:

EXAMPLE 1

140 parts of citric acid having a particle size of 0.2-0.3 mm are mixed in a mixer, preferably already at 60° C., with 2 parts of a concentrated solution of monosodium citrate and are moistened. 85 parts of fine sodium bicarbonate are then added and the mixture is allowed to undergo an initial reaction.

50 parts of magnesium trisilicate and 5 parts of maltodextrin are then added and are allowed to become distributed over the partially reacted mixture with vibratory mixing. 50 parts of potassium carbonate are then added and the mixing speed is reduced in order to maintain the particulate structure of the mass.

Drying is then carried out at a high temperature with a powerful air current in a high-speed dryer or preferably with the application of a high vacuum in a vacuum mixer.

The product formed is milled to a particle size of 0.5-1 mm and, after the addition of sweetener and flavors, is either used as effervescent granules or compressed to give tablets.

EXAMPLE 2

140 parts of citric acid, 85 parts of sodium carbonate, 50 parts of magnesium trisilicate and 8 parts of galactomanan are mixed in the dry state, preferably heated to 60° C., and a concentrated solution of 2 parts of trisodium citrate are added. The reaction begins slowly and the reaction mixture is mixed until a lumpy structure is formed and is then dried immediately either by means of a hot air current or preferably by the use of a vacuum. The end product is further processed as in Example 1.

EXAMPLE 3

140 parts of citric acid are moistened with 2 parts of a concentrated trisodium citrate solution and are mixed with 110 parts of sodium bicarbonate and 100 parts of sucralfate at room temperature or preferably at 60° C. The sucralfate slows down the resulting reaction very markedly, and excellent granules are formed.

These are dried as in Examples 1 and 2, either by means of a dry air current at a high temperature or preferably in vacuo, if necessary a desired amount of sweeteners and/or flavors is added and the mixture is sieved to a particle size of 0.5-1 mm and either used as granules or compressed to give tablets which may contain 1000 mg of sucralfate per tablet.

EXAMPLE 4

140 parts of citric acid, 85 parts of sodium bicarbonate, 50 parts of magnesium trisilicate and 20 parts of aluminum hydroxide are mixed and are reacted with 2 parts of a monosodium citrate solution. After the reaction, 60 parts of potassium bicarbonate are added. After the formation of granules, 10 to 20 parts of maltodextrin are added, with the result that the reaction virtually stops.

Further processing of the resulting granules is carried out as in Example 1 or 3.

Depending on the tablet size, doses of 200 to 1000 mg of magnesium trisilicate per tablet are achieved.

In all Examples, tablet hardnesses of up to 15 kp can be achieved during compression. Tablet hardnesses of 10 kp result in a dissolution time of 90 to 120 seconds, the insoluble active substance remaining suspended without a residue for 5-10 minutes in a drink of about 100-150 ml of water.

EXAMPLE 5

A mixture of 850 parts of citric acid, 1550 parts of sodium bicarbonate and 100 parts of tragacanth is granulated with alcohol or with trisodium citrate solution, dried (vacuum dried) and, after drying, mixed with 300 parts of bismuth subcarbonate.

The tablets are compressed on a tablet press to give tablets weighing 2.8 g and having a hardness of 8-10 kp; they have a dissolution time of about 100 seconds in about 60-100 ml of water.

EXAMPLE 6

850 parts of citric acid, 550 parts of sodium carbonate, 500 parts of calcium carbonate and 100 parts of maltodextrin are mixed, granulated with 50% alcohol or monocalcium citrate solution and dried (vacuum dried), 300 parts of bismuth carbonate are added and the mixture is compressed to give tablets.

EXAMPLE 7

850 parts of citric acid, 300 parts of sodium bicarbonate, 500 parts of potassium carbonate and 400 parts of calcium carbonate are mixed, granulated with 50% alcohol or buffer solution and vacuum dried. 300 parts of bismuth subcitrate (complex potassium bismuth citrate) are added and the mixed is compressed to give tablets weighing 2.4 g. These tablets dissolve as a complex in water and are an alternative to the conventional soluble bismuth salts.

EXAMPLE 8

850 parts of citric acid, 300 parts of sodium bicarbonate, 500 parts of potassium carbonate and 400 parts of calcium carbonate are mixed, granulated with a buffer solution and vacuum dried at 60° C. down to about 50 mbar. 300 parts of the complexed 3-potassium bismuth 2-citrate are then added and the mixture is heated at 70° C. in vacuo. As the complex salt may contain up to 8% of water, this vacuum treatment results in a reduction in the water content, corresponding to the vapor pressure of water at 60° or 70° C. Consequently, sufficient residual moisture remains to ensure that the potassium bismuth citrate dissolves; on the other hand, however, the moisture content is reduced to such an extent that the effervescent tablet produced subsequently by compression remains stable to 50° C. even under tropical conditions, and no chain reaction occurs.

The tablets are compressed to 2.4 g and correspond to 120 mg of $Bi_2O_3$. These tablets dissolve in water to give a clear solution and are a further alternative to the conventional soluble bismuth preparations.

EXAMPLE 9

1 g of the active substance to be investigated was added to 100 ml of simulated gastric juice (0.1N HCl, pH 1.12). The pH was measured at 10 sec intervals while stirring.

| Active substance | Acid-binding power | pH after 20 sec | 120 sec |
|---|---|---|---|
| Magnesium oxide | 46.8 meq/g | 9.68 | 10.18 |
| Magnesium trisilicate | 7.6 meq/g | 1.15 | 1.20 |
| Bismuth subcarbonate | 2.4 meq/g | 1.13 | 1.17 |
| Bismuth subcitrate | 3.7 meq/g | 1.18 | 1.22 |
| Sucralfate | 15.9 meq/g | 1.15 | 1.20 |

In contrast to magnesium oxide, magnesium trisilicate and sucralfate take up the acids substantially more slowly. After 120 sec, the reaction with magnesium oxide has ended whereas in the case of magnesium trisilicate and sucralfate the pH has changed only by 0.2 unit. A change by 0.2 pH unit is detectable in the case of magnesium oxide after only 10 sec.

We claim:

1. A preparation of granules containing at least one insoluble, complexed or slightly insoluble acid-binding substance in powder form and an effervescent system consisting of at least one organic, edible acid and at least one alkali metal or alkaline earth metal carbonate or bicarbonate, wherein said preparation is a pharmaceutical preparation which binds gastric acid and in which the substance is an active substance and each granule contains at least one acidic component, at least one carbonate component and at least one active substance bonded to one another, the active substance being present in an amount of 5 to 50% by weight, having an acid-binding power of 2 to 40 meq/g, not reacting with the acid of the effervescent system and increasing the pH and in 0.1N HCl during 2 min by a maximum of 0.5, and each granule containing a core as a carrier comprising crystals of the edible, organic acid on which the active substance powder particles, are anchored.

2. A preparation as claimed in claim 1, wherein a binder layer
    of a reaction product of at least one acidic with at least one carbonate component or
    of a hydrocolloid
is provided for binding the granule components to one another or for binding the powder mixture to the core.

3. A preparation as claimed in claim 1, wherein the active substance is at least one of magnesium trisilicate, sucralfate and a bismuth salt.

4. A preparation as claimed in claim 1, wherein the effervescent preparation is sodium-free or has a low sodium content.

5. A preparation as claimed in claim 2, wherein the active substance is at least one of the compounds magnesium trisilicate, sucralfate and a bismuth salt.

6. A preparation as claimed in claim 2, wherein the effervescent preparation is sodium-free or has a low sodium content.

7. A preparation as claimed in claim 3, wherein the effervescent preparation is sodium-free or has a low sodium content.

8. A preparation as claimed in claim 1, wherein the active substance is present in an amount of 8 to 30% by weight.

9. A preparation as claimed in claim 8, wherein the active substance is present in an amount of 12 to 25% by weight.

10. A preparation as claimed in claim 1, wherein the acid binding power is 3.5 to 25 meq/g.

11. A preparation as claimed in claim 1, wherein the acid is citric acid.

12. A preparation as claimed in claim 1, wherein the powder particles of the active substance are present in mixture with at least one part of the carbonate components in powder form.

13. A preparation as claimed in claim 1, wherein the active substance powder particles are on the carrier with the aid of a binder layer.

14. A preparation as claimed in claim 2, wherein the hydrocolloid is at least one of xanthan, maltodextran, galactomanan and tragacanth.

15. A preparation as claimed in claim 1, wherein the active substance is present in an amount of 12 to 25% by weight, the acid binding power is 3.5 to 25 meq/g and the edible organic acid is citric acid.

16. A preparation as claimed in claim 1, wherein the granules are present in the form of a compressed tablet.

* * * * *